(12) United States Patent
Kim (10) Patent No.: US 8,277,216 B2
(45) Date of Patent: Oct. 2, 2012

(54) METHOD AND APPARATUS FOR PREPARING DENTURE

(76) Inventor: Tae Hyung Kim, La Canada, CA (US)

(*) Notice: Subject to any disclaimer, the term of this patent is extended or adjusted under 35 U.S.C. 154(b) by 32 days.

(21) Appl. No.: 12/782,663

(22) Filed: May 18, 2010

(65) Prior Publication Data
US 2010/0297572 A1 Nov. 25, 2010

Related U.S. Application Data (60) Provisional application No. 61/179,698, filed on May 19, 2009.

(51) Int. Cl.
A61C 9/00 (2006.01)
(52) U.S. Cl. ............................................ 433/37; 433/41
(58) Field of Classification Search .................. 433/17, 433/34, 43, 201.1, 214, 37, 41; 264/17; 128/862
See application file for complete search history.

(56) References Cited

U.S. PATENT DOCUMENTS

| 4,145,812 A | * | 3/1979 | Johnson et al. | ................. 433/41 |
| 4,543,062 A | * | 9/1985 | Lee | .................. 433/71 |
| 4,657,509 A | * | 4/1987 | Morris | ............................. 433/37 |
| 4,789,334 A | * | 12/1988 | Wedenig et al. | ................. 433/37 |
| 5,186,624 A | * | 2/1993 | Gottsleben | ....................... 433/69 |
| 6,196,840 B1 | * | 3/2001 | Zentz et al. | ...................... 433/71 |
| 2003/0180681 A1 | | 9/2003 | Kwon et al. | |
| 2007/0190492 A1 | * | 8/2007 | Schmitt | ......................... 433/213 |
| 2008/0254406 A1 | | 10/2008 | Wagner | |

FOREIGN PATENT DOCUMENTS

KR 10-2009-0036643 4/2009
WO 02-00134 1/2002

* cited by examiner

Primary Examiner — Cris L Rodriguez
Assistant Examiner — Matthew Seward
(74) Attorney, Agent, or Firm — Lee, Hong, Degerman, Kang & Waimey (57) ABSTRACT

A dental impression tray assembly includes an upper tray and a lower tray operable with the upper tray, and the lower tray includes a first piece configured to measure jaw relations of a patient's mouth and a pair of second pieces detachably attachable to the first piece. The first piece of the lower tray is inserted into the patient's mouth independently of the pair of second pieces of the lower tray to measure the jaw relations and to obtain a bite registration. After the first piece is connected to the pair of second pieces, the assembly allows a final gum impression of the patient's lower gum to be obtained.

23 Claims, 6 Drawing Sheets

METHOD AND APPARATUS FOR PREPARING DENTURE

CROSS REFERENCE TO RELATED APPLICATIONS

Pursuant to 35 U.S.C. §119(e), this application claims the benefit of earlier filing date and right of priority to Provisional Application No. 61/179,698 filed on May 19, 2009, the contents of which are hereby incorporated by reference herein in their entirety.

FIELD OF THE INVENTION

The present disclosure relates generally to dentures, and more particularly to a simplified method and apparatus for fabricating dentures. In particular, the present invention is directed to reducing a number of visits required for fabrication of a denture without compromising the quality of the denture by using the inventive method and apparatus.

DESCRIPTION OF THE RELATED ART

Complete dentures are constructed to replace missing teeth for patients who are fully edentulous. Fabrication of a set of complete dentures is a challenging task for any dentist. Complete dentures should be comfortable when inserted into the mouth of a patient. Therefore, impressions of edentulous patients must be accurate, duplicating all the details of the oral tissues. Imperfection in the impression affects the fit of the dentures, and thus, may cause serious effects when wearing the dentures.

Dentures are conventionally constructed and fitted by dentists with the assistance of dental technicians using a flask investment technique. This complex process requires measurements of masticatory function, impressions of the gum and surrounding tissues of the affected area, study models and working models, and a series of back and forth steps between the dentist and the dental technician to manufacture the denture. The entire process of constructing dentures using conventional methods and devices requires a number of appointments between the dentist and the patient, and involves a significant amount of time and skill.

Generally, a patient must make a plurality of visits to a dentist to make a set of dentures. Such visits are necessary in order for a dentist to take an impression of the patient's gums, as well as a bite registration of the patient's jaw position and vertical dimension.

For example, during a first visit, a dentist examines a patient and takes a preliminary alginate impression of the patient using stock trays. After the preliminary alginate impression is taken on the impression material, the impression tray is delivered to a laboratory. In the laboratory, plaster is poured onto the preliminary alginate impression to form accurate models of the shape of the edentulous ridges. The preliminary alginate impression is used to make custom fitting impression trays for a final impression.

During a second visit, the dentist checks and adjusts the custom fitting impression trays as necessary and takes the final impression. Afterwards, in the laboratory, a master model is created and a base plate is fabricated based on the final impression received from the dentist. Then, a bite registration rim or block, usually made of wax, is fabricated from the master gum mold. The master gum mold, with the bite registration rim attached thereto, is sent back to the dentist.

During a third visit, the bite registration rim is inserted into the mouth of the patient, and adjusted inside the mouth to determine maxilla-mandibular relations and to take a bite registration. Further, artificial teeth to be used for the denture are selected by the dentist and the patient. The adjusted bite registration rim is sent back to the laboratory to fabricate a wax try-in. The laboratory returns the wax try-in with the actual final teeth lined up along the outer edge of the wax rim. The wax try-in looks similar to a real denture except that the base fits loosely on the gums and the teeth are embedded in wax instead of plastic.

During a fourth visit, the dentist examines how the wax try-in looks and works in the patient, checking occlusal and vertical dimension. If adjustments are necessary, the wax try-in can be sent back to the laboratory to reset the teeth. If no adjustments are needed, the wax try-in is sent back to the laboratory to be processed and finished. In the laboratory, the existing base and wax are discarded, and replaced by a tightly fitting plastic denture base.

During a fifth visit, the finished denture is then inserted into the mouth of the patient and adjusted as needed. The denture is also checked for occlusion and corrected, if necessary. As discussed above, it may generally take at least four or more visits of a patient until the finished dentures are finally inserted into the mouth of the patient. Thus, the multi-step process of preparing a set of dentures, requiring several iterations between the dentist and the dental laboratory is time-consuming, labor intensive and costly.

Moreover, difficulties exist in producing a good quality denture due to the great diversity in sizes and shapes of patients' mouths, and facial features requiring custom fabrication of each denture. Thus, standardization of prefabricated dentures is very difficult. Proposals to overcome the shortcomings of the conventional methods, such as multiple visits, intensive labor, and laboratory time needed for the fabrication of dentures, have had little success.

The shortcomings of prior proposals to overcome some of the difficulties in producing a conventional custom denture include: (1) Difficulty in collecting all necessary data to fabricate a high quality denture during one visit using the conventional method; (2) Difficulty in taking an impression and measuring jaw relations together in the conventional tray; (3) Expense, complexity and length of the procedure; (4) Skill level required; (5) Poor fit to the bite of an individual patient; (6) Excessive thickness or thinness of the denture base; (7) Use of articulated models, plaster and wax; (8) Poor fit to the tissue area of an individual patient; and (9) Poor functionality. Therefore, there is a need for a method and apparatus that will reduce the length of the procedure, and the number of times the patient visits the dentist for fabrication of a denture while providing a perfect fit of the denture to the patient.

SUMMARY OF THE INVENTION

The present invention overcomes all of the aforementioned shortcomings by providing a dental device that is convenient for a health professional to manipulate and software that allows accurate manufacturing of a complete denture without intensive manual labor. The present invention reduces the number of patient visits, cost and time conventionally required to produce a custom denture.

In accordance with one embodiment of the present invention, a dental impression tray assembly includes an upper tray and a lower tray operable with the upper tray, the lower tray including a first piece configured to measure jaw relations of a patient's mouth and a pair of second pieces detachably attachable to the first piece, wherein the first piece is inserted into the patient's mouth independently of the pair of second pieces to measure the jaw relations and to obtain a bite registration, and wherein the assembly is configured to allow a final gum impression of the patient's lower gum to be obtained after the first piece is connected to the pair of second pieces.

In accordance with another embodiment of the present invention, a method of measuring jaw relations and a final gum impression of a patient's mouth during a patient's single visit to a dentist using a dental impression tray assembly including a lower tray and an upper tray to fabricate a denture includes inserting a first piece of the lower tray into the patient's mouth, measuring the jaw relations using the first piece, attaching a pair of second pieces of the lower tray to the first piece after measuring the jaw relations, inserting the assembled first piece and the pair of second pieces into the patient's mouth, and obtaining the final gum impression of the patient's mouth.

These and other embodiments will also become readily apparent to those skilled in the art from the following detailed description of the embodiments having reference to the attached figures, the invention not being limited to any particular embodiment disclose.

BRIEF DESCRIPTION OF THE DRAWINGS

The above and other aspects, features, and advantages of the present invention will become more apparent upon consideration of the following description of preferred embodiments, taken in conjunction with the accompanying drawings.

DETAILED DESCRIPTION OF PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1A:
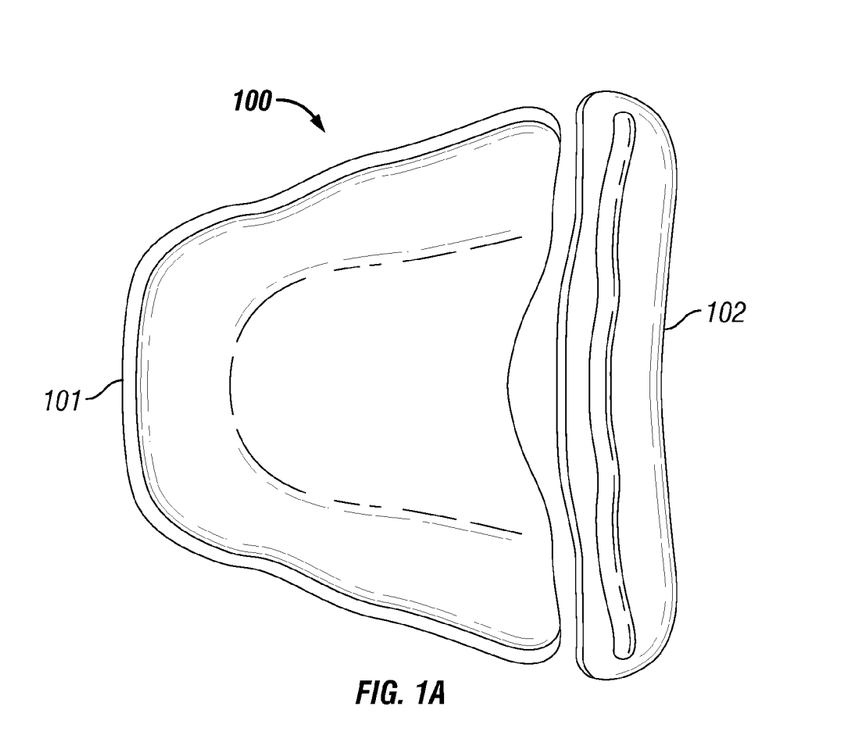
FIG. 1A is a top view of an upper tray according to an embodiment of the present invention, the upper tray comprising a first center piece and an outer piece where the first center piece and the outer piece are separated.
Figure 1B:
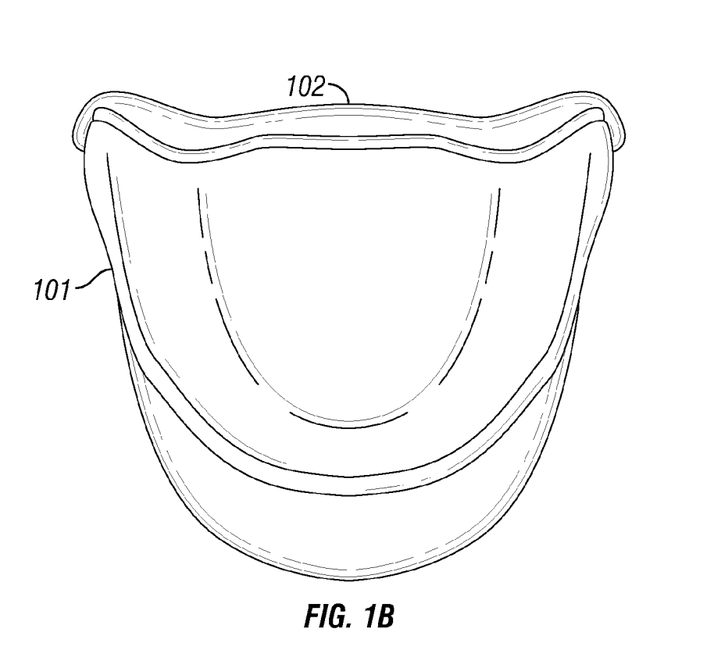
FIG. 1B is a top view of the upper tray where the first center piece and the outer piece are combined.
Figure 1C:
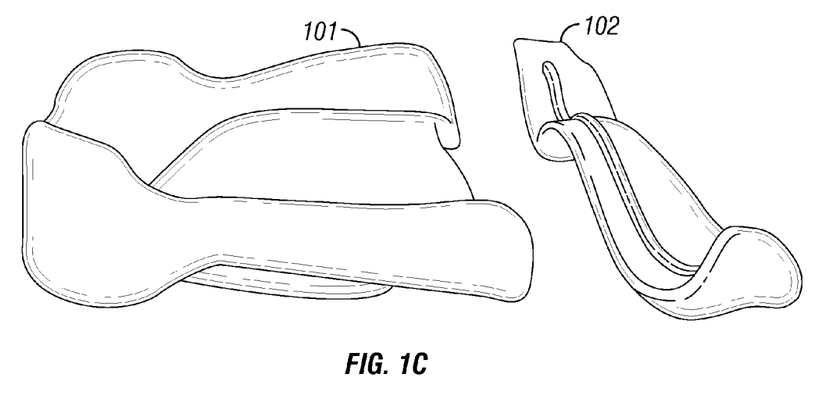
FIG. 1C is a disassembled perspective view of the upper tray.
Figure 1D:
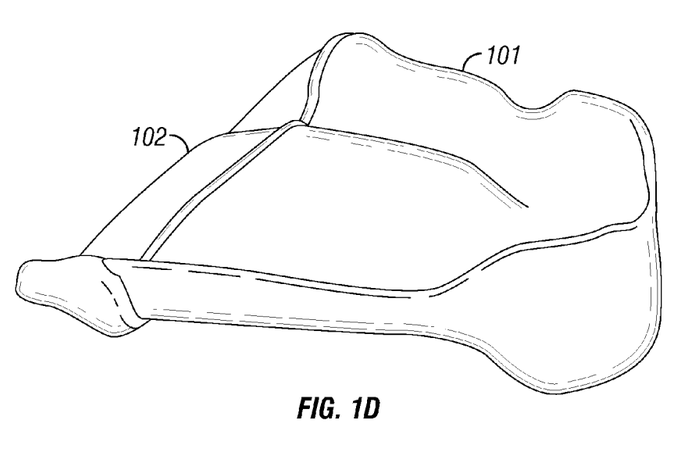
FIG. 1D is an assembled perspective view of the upper tray.
Figure 2A:
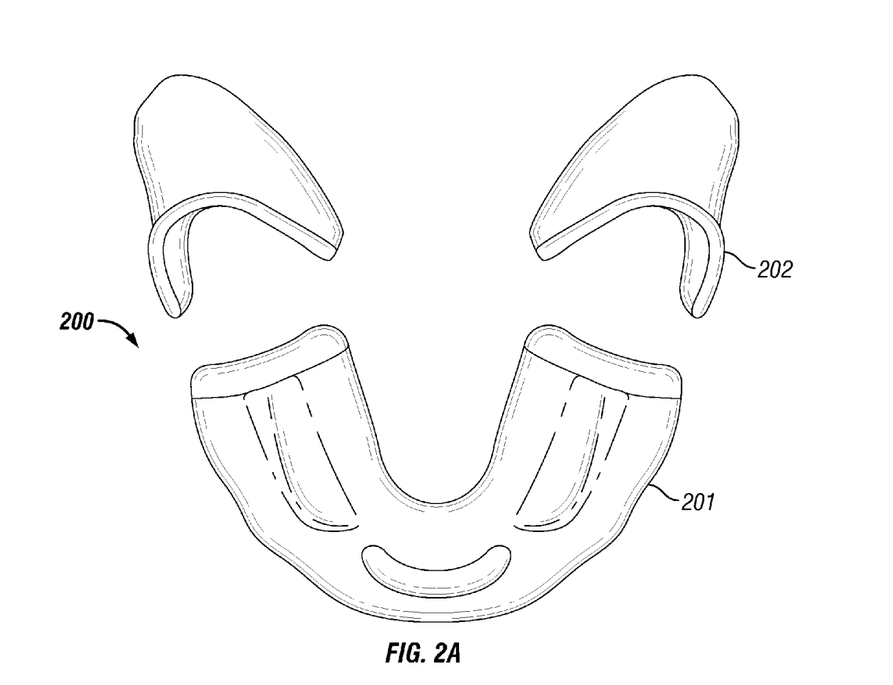
FIG. 2A is a top view of a lower tray according to an embodiment of the present invention, the lower tray comprising a second center piece and a pair of back pieces where the second center piece and the pair of back pieces are separated.
Figure 2B:
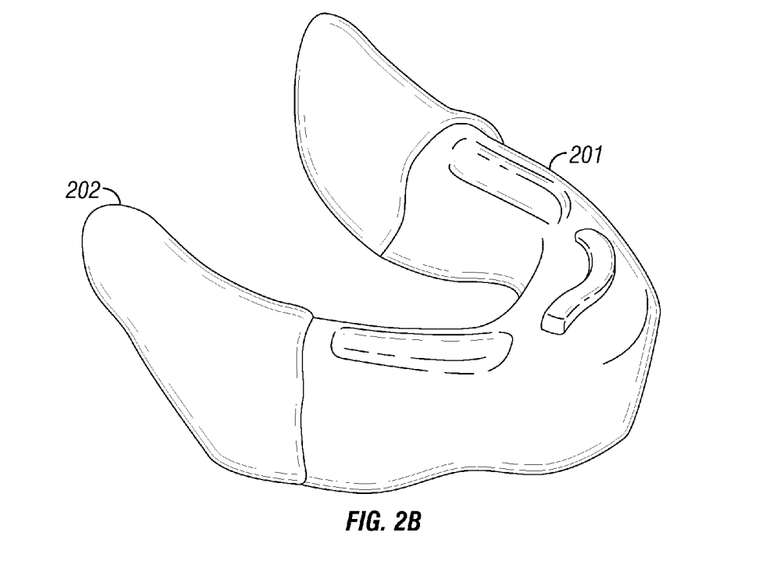
FIG. 2B is a perspective view of the lower tray in which the second center piece and the pair of back pieces are assembled.
Figure 2C:
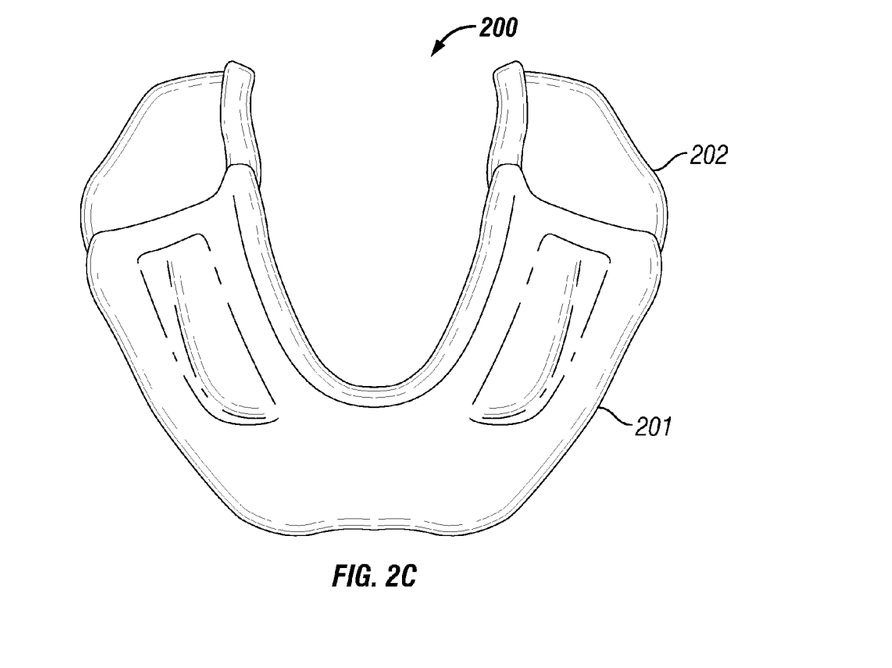
FIG. 2C is a bottom view of the lower tray in which the second center piece and the pair of back pieces are assembled.

According to an embodiment of the present invention, the inventive set of trays, including an upper tray 100 and a lower tray 200, are capable of measuring jaw relations and taking a final impression in a single visit. The set of trays 100 and 200 may be made of plastic and may be available in various sizes to accommodate different sizes of jaws. The set of trays 100 and 200 may include a plurality of pieces or portions that can be assembled or disassembled. The upper tray 100 may be formed as a single piece rather than two pieces 101 and 102 as shown in FIGS. 1A-1D. The lower tray 200 comprises a plurality of pieces 201 and 202 as shown in FIGS. 2A-2B to be accommodated in a mouth of a patient.

A first center piece 101 of the upper tray 100 and a second center piece 201 of the lower tray 200, as shown in FIGS. 1A-1D and FIGS. 2A-2B, respectively, are used to take jaw relations, such as a vertical dimension (VD) and a centric relation (CR). For example, the first and second center pieces 101 and 201 receive a polymer material and the first and second center pieces retaining the polymer material are individually inserted into the mouth to obtain a first impression or a partial impression of a patient's gum including about two-thirds of the gums including the anterior gums. If the upper tray 100 is formed of only a single piece, the final impression of the upper gum may be obtained at once, the first impression becoming the final impression for the upper gum.

Figure 3A:
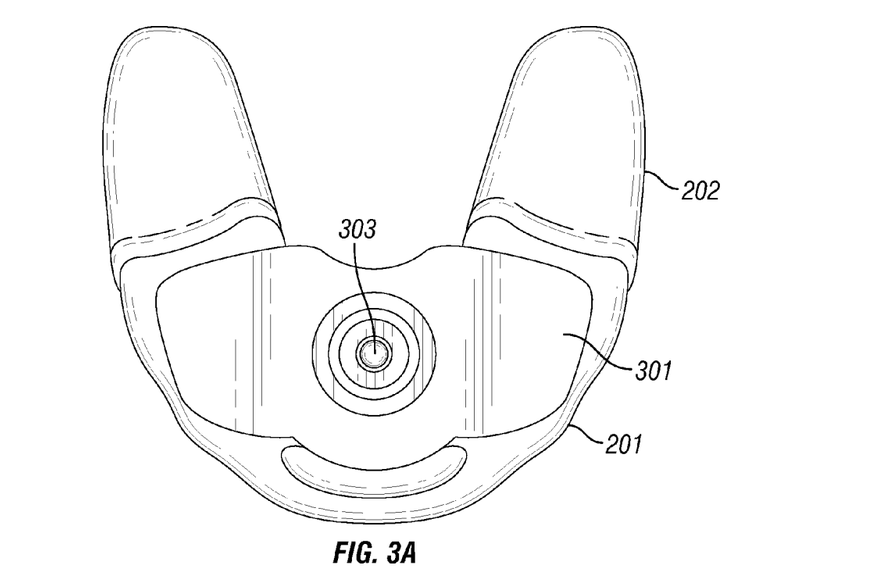
FIG. 3A is a top view of the assembled lower tray to which an intra-oral tracer is attached according to an embodiment of the present invention.
Figure 3B:
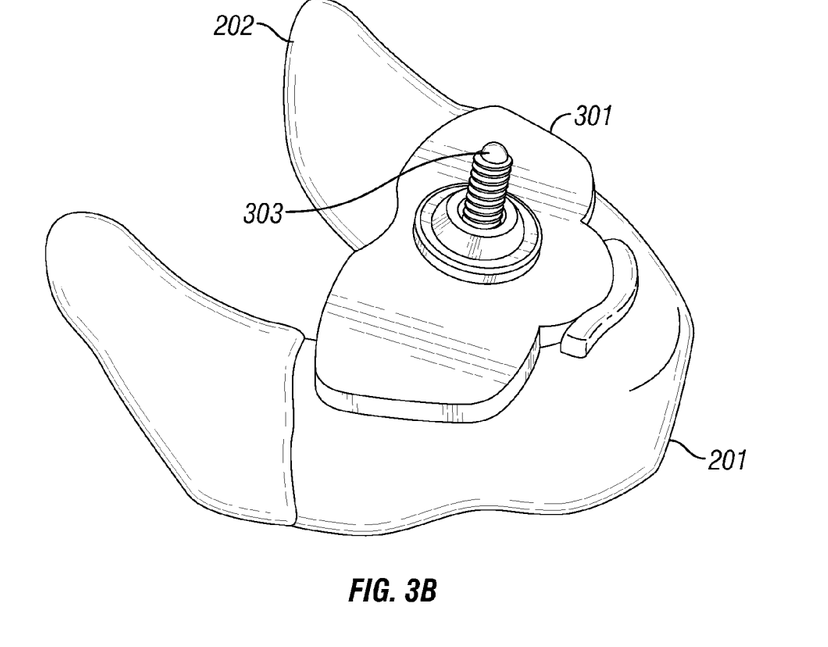
FIG. 3B is a perspective view of the assembled lower tray to which the intra-oral tracer is attached.
Figure 4:
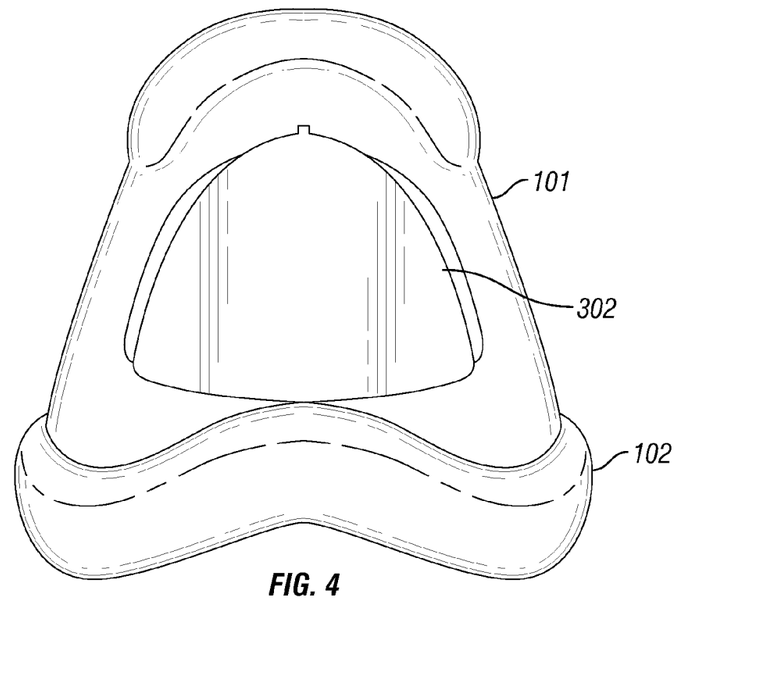
FIG. 4 is a bottom view of the assembled upper tray to which a cover to be contacted by the intra-oral tracer is attached.
Figure 5A:
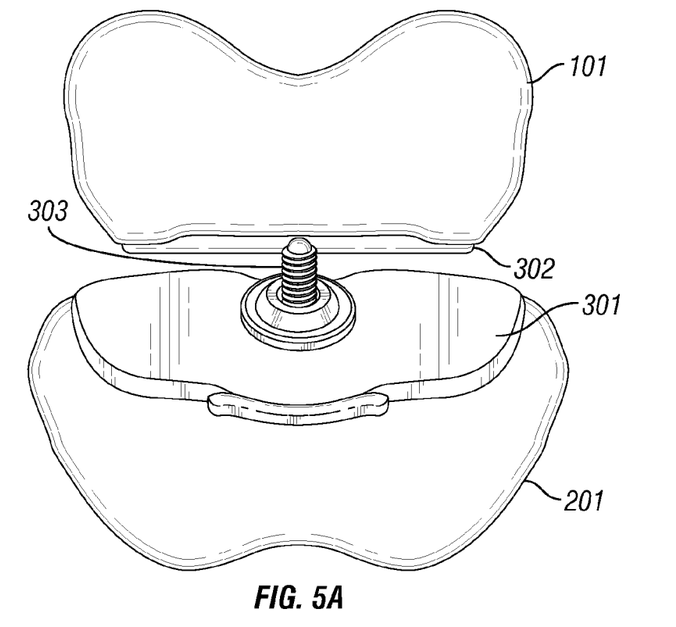
FIG. 5A is a frontal view of the first center piece of the upper tray with the cover and the second center piece of the lower tray with the intra-oral tracer, the intra-oral tracer contacting the cover.
Figure 5B:
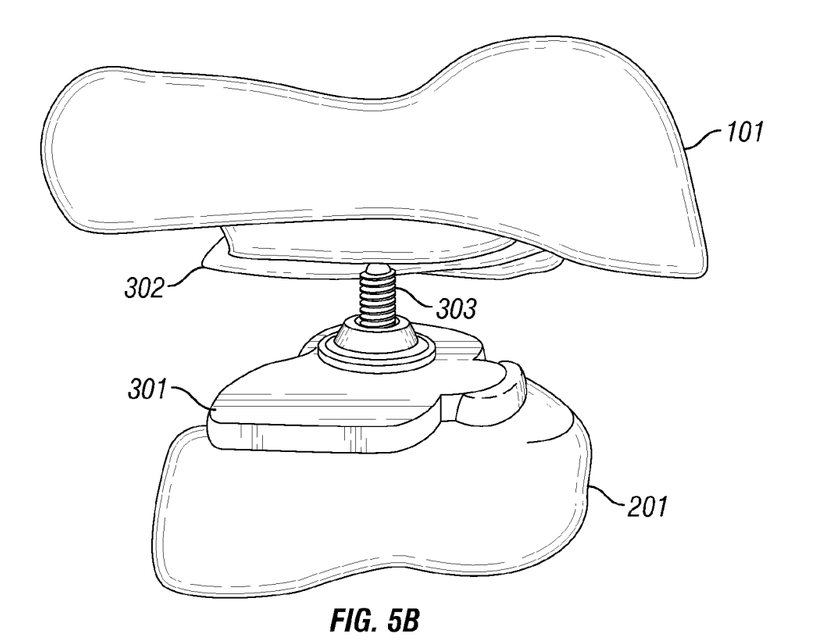
FIG. 5B is a side view of the first center piece of the upper tray with the cover and the second center piece of the lower tray with the intra-oral tracer, the intra-oral tracer contacting the cover.

Once the first impression is obtained, the first and second center pieces 101 and 201 retaining the partial impression are inserted into the mouth together with an intra-oral tracer 301 placed between the first center piece 101 and second center piece 201 as shown in FIGS. 5A and 5B. For example, the intra-oral tracer 301 may be inserted into an upper surface of the second center piece 201 of the lower tray 200 as shown in FIGS. 3A and 3B and a cover 302 may be placed on a lower surface of the first center piece 101 of the upper tray 100 as shown in FIG. 4. The upper piece 100 and the lower piece 200, as shown in FIGS. 5A and 5B, are inserted into the mouth together to measure jaw relations. When the upper tray 100 and the lower tray 200 are inserted into the mouth, the outer piece 102 and the pair of back pieces 202 are not attached to the first center piece 101 and the second center piece 201, respectively. Jaw relations are measured by lowering or raising the screw 303 of the intra-oral tracer 301 in the mouth to contact the cover 302. Once the intra-oral tracer 301 is adjusted to be in a clinically acceptable position, a polymer material is filled in between the upper tray 100 and the lower tray 200 to obtain a bite registration.

After measuring the jaw relations with the first and second center pieces 101 and 201, the first and second center pieces are connected to their respective extension pieces, including the outer piece 102 and the pair of back pieces 202, such that the assembled upper and lower trays 100 and 200 are used to take the final impression. Thus, according to the present disclosure, a jaw relation record is measured with the first and second center pieces 101 and 201 before the final impression is taken with the complete or assembled upper and lower trays 100 and 200 also including the outer piece 102 and the pair of back pieces 202.

In order to measure the jaw relation record, the mouth of the patient needs to be able to accommodate the trays when they are inserted into the mouth. However, if full-sized trays, such as conventional trays, are inserted into the mouth, it is practically impossible for the patient's mouth to accommodate the full-sized conventional trays because the end portions of the upper and lower trays contact each other at the posterior position of the mouth, thus becoming very bulky in the mouth. In order to solve this problem, the trays of the present invention have been sized to be accommodated in the mouth. For example, the dissembled trays, or a full sized upper tray and the dissembled lower tray, cover at least an anterior position of the mouth while not covering the entire region of the mouth.

Referring to FIGS. 5A-5B, the first and second center pieces 101 and 201 play a role of record base to capture the partial impression intra-orally. Further, the first and second center pieces 101 and 201 also function as a conventional record base to allow the dentist to position the jaw and determine the VD, thus allowing assessment and measurement of the height and position of the jaw. The intra-oral tracer 301 can be adjusted until the patient's mouth is in a clinically acceptable position. From this, the VD can be defined and the CR position can be located. After determining the CR position using the intra-oral tracer 301, the position is captured using PVS (polyvinylsiloxane) material. The first and second center pieces 101 and 201 are then removed from the mouth and each center piece 101 and 201 becomes the positioning guide for the final impression.

The shapes of the trays have unique dimensions, the first center piece 101 providing the position of the tray and the second center piece 201 supporting the borders and capturing muscle movements. The first and second center pieces 101 and 201 may have openings to retain the impression material.

According to another embodiment of the present invention, software is used to obtain a virtual model of the denture to be fabricated. From the scanned data of the PVS impression of the upper and lower trays 100 and 200 and the final impression, a three-dimensional (3-D) model is generated in a computer. The inventive software is used to fabricate dentures by taking the measurements of edentulous regions of the maxilla and mandible from the respective impressions. Further, information on the VD and CR obtained by using the inventive tray assembly is input into the software to create the dentures. The software synthesizes all the data and creates a 3-D model of the edentulous ridge and generates the placement of the teeth and gingival tissue. Included in the software are various sets of teeth types, varying based on shape, size and color. After selecting a desired tooth type, the software automatically generates a denture with the above discussed three reference points to correctly place the teeth. Furthermore, the software corrects any overlap of tooth structure that may arise from a discrepancy between the selected tooth type and the measurements entered from the impressions and gathered data. Once the virtual denture is created, the software will export the file to allow fabrication of the custom denture.

According to yet another embodiment of the present invention, the final denture is milled based on the above described information. Upon receiving the file of the virtual denture generated by the software, a machine will mill an acrylic block into the real denture. The milling denture comprises two different pieces. The first piece is on the teeth portion, and the second piece is on the gingival portion. Each piece is milled separately, and after milling, the two pieces are put together to form the denture.

Alternatively, the denture may be fabricated by rapid prototyping or a combination of the rapid prototyping and a conventional flasking technique. This allows different colors to be used to represent gingival and teeth colors in one operation, using the colors from the rapid prototyping, which are derived from the model.

The present disclosure relates to the art and science of dental prosthetics whereby dental professionals can produce a high quality complete denture at a substantially reduced cost, and in a reduced time, by using newly invented devices and software. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A dental impression tray assembly comprising:
    an upper tray sized to be inserted into a patient's mouth after the upper tray receives impression material to take a first impression of a patient's gum; and
    a lower tray comprising:
        a first piece sized to be inserted into the patient's mouth after the first piece receives impression material to take a second impression of the patient's gum, wherein the first piece is curved at about a central portion to form a right end portion and a left end portion; and
        a pair of second pieces detachably coupled to the first piece, a right piece of the pair of second pieces coupled to the right end portion of the first piece and a left piece of the pair of second pieces coupled to the left end portion of the first piece, wherein a size of the lower tray is consistent when the pair of second pieces are coupled to the first piece,
    wherein the pair of second pieces are configured to fit over the patient's gum when the pair of second pieces are coupled to the first piece,
    wherein the second impression is obtainable after the first piece is inserted into the patient's mouth with the pair of second pieces attached,
    wherein the pair of second pieces are detachable from the first piece after the second impression is obtained, and the upper tray retaining the first impression and the first piece of the lower tray retaining the second impression are insertable together into the mouth to determine jaw relations comprising a vertical dimension and a centric relation,
    wherein a gap formed between the upper tray retaining the first impression and the first piece of the lower tray retaining the second impression is sized to receive bite registration material to obtain a bite registration, and
    wherein a further impression of the patient's gum is obtainable when the pair of second pieces are re-attached to the first piece and at least the lower tray is insertable into the mouth after the second pieces receive impression material.

2. The assembly of claim 1, further comprising an intra-oral tracer that is configured to be detachably coupled to the first piece of the lower tray and inserted into the mouth to be placed between the upper tray and the first piece of the lower tray and to measure the vertical dimension and the centric relation.

3. The assembly of claim 2, wherein the intra-oral tracer comprises an adjusting member that is inserted into the hole and adjustable to be raised or lowered to determine the vertical dimension and to adjust a size of the gap for receiving the bite registration material.

4. The assembly of claim 2, wherein the first piece of the lower tray is sized to cover an anterior portion of the patient's lower gum and the pair of second pieces are sized to cover distal portions or the rest of the lower gum when attached to the first piece and the entire lower tray is inserted into the patient's mouth.

5. The assembly of claim 1, wherein the assembly is made of plastic.

6. The assembly of claim 1, wherein the upper tray comprises:
a third piece configured to measure the jaw relations of the patient's mouth along with the first piece of the lower tray,
wherein the third piece is sized to cover the patient's upper anterior gum and have a front portion and a rear portion.

7. The assembly of claim 6, wherein the third piece is further configured to allow the first impression of the patient's upper anterior gum to be obtained.

8. The assembly of claim 6, wherein the upper tray further comprises:
a fourth piece configured to be detachably coupled to the rear portion of the third piece,
wherein the first impression is obtained when the third piece is inserted into the patient's mouth with the fourth piece attached after the third piece receives impression material,
wherein the fourth piece is configured to be detached from the third piece after obtaining the first impression, and the third piece retaining the first impression and the first piece of the lower tray retaining the second impression are inserted together into the mouth to determine the jaw relations, and
wherein the further impression is obtained when the fourth piece is re-attached to the third piece and the upper tray and the lower tray are configured to be inserted together into the mouth after the fourth piece receives the impression material.

9. The assembly of claim 8, wherein the fourth piece of the upper tray is sized to cover a distal portion or the rest of the patient's upper gum when attached to the third piece.

10. The assembly of claim 1, wherein the assembly is configured to allow the bite registration and final gum impressions, comprising the first impression, the second impression, and the further impression, to be obtained during a patient's single visit to a dentist without requiring heat treatment of the upper tray and the lower tray.

11. The assembly of claim 6, wherein the upper tray is configured to contact an upper gum or jaw area of the patient's mouth and the lower tray is configured to contact a lower gum or jaw area of the patient's mouth.

12. The assembly of claim 1, wherein the jaw relation is determined and the bite registration is taken before the further impression of the patient's gum is obtained.

13. The assembly of claim 1, wherein final gum impressions, comprising the first impression, the second impression, and the further impression, are scanned and an image of the scanned final gum impressions is used to fabricate a denture using software.

14. The assembly of claim 1, wherein each of the pair of second pieces is formed as a single body with a first connecting portion which allows stable coupling to a second connecting portion of the first piece.

15. The assembly of claim 14, wherein one of the first connecting portion and the second connecting portion has a slot structure configured to receive the other one of the first connecting portion and the second connection portion such that the other one of the first connecting portion and the second connecting portion is inserted into the slot structure of the one of the first connecting portion and the second connecting portion.

16. The assembly of 1, wherein the intra-oral tracer is coupled to the first piece such that an open space of the curved area is substantially covered by the intra-oral tracer.

17. The assembly of claim 2, wherein a connecting portion of the intra-oral tracer is inserted into a receiving portion of the first piece such that the intra-oral tracer is coupled to the first piece to be inserted together with the upper tray into the mouth.

18. The assembly of claim 17, wherein the impression material is received at a first side of the first piece and the connecting portion of the intra-oral tracer is located at a portion of a second side which is the other side of the first piece.

19. The assembly of claim 4, wherein a total length of the entire lower tray including the first piece and the pair of second pieces is substantially the same as a sum of a length of the first piece and lengths of the pair of second pieces.

20. The assembly of claim 19, wherein the total length of the entire lower tray is always the same.

21. A dental impression tray assembly comprising:
a lower tray configured to receive impression material to permit taking a first impression of a patient's lower gum and comprising a first piece and a pair of second pieces detachably coupled to the first piece, wherein the first piece comprises a receiving structure and the pair of second pieces are configured to fit over the patient's lower gum when the pair of second pieces are coupled to the first piece;
an upper tray configured to receive impression material to permit taking a second impression of the patient's upper gum and comprising a third piece and a fourth piece configured to be detachably coupled to the third piece, wherein the third piece and the fourth piece are configured to be combined and inserted together into a mouth of the patient to take the second impression capturing the upper gum of the patient; and
an intra-oral tracer that is configured to be detachably coupled to the first piece of the lower tray via the receiving structure such that the intra-oral tracer coupled to the first piece is placed between the third piece of the upper tray and the first piece of the lower tray when the third piece and the first piece are inserted into the mouth together, the intra-oral tracer comprising a hole and an adjustable member that is inserted into the hole to be raised or lowered through the hole to determine a vertical dimension,
wherein the first piece of the lower tray is sized to cover an anterior portion of the patient's lower gum and the pair of second pieces are sized to cover distal portions or the rest of the lower gum when attached to the first piece such that a size of the lower tray including the first piece and the pair of second pieces is fixed,
wherein the pair of second pieces are configured to be detached from the first piece and the fourth piece is configured to be detached from the third piece after taking the first impression and the second impression, respectively, and the first piece of the lower tray with the intra-oral tray attached and the third piece of the upper tray are configured to be inserted together into the mouth to determine jaw relations comprising the vertical dimension and a centric relation.

22. A dental impression tray assembly comprising:
a lower tray configured to receive impression material and comprising a first piece and a pair of second pieces, wherein:
- the first piece, which is substantially U-shaped, is sized and configured to fit over at least an anterior portion of the lower gum, the first piece comprising a receiving portion,
- each of the pair of second pieces, which is configured to be detachably coupled to each of two end portions of the substantially U-shaped first piece, is sized and configured to fit over a posterior portion of the lower gum when the pair of second pieces are coupled to the first piece, and
- the first piece is configured to be inserted into a patient's mouth with the pair of second pieces attached or without the pair of second pieces attached;

an upper tray configured to receive impression material and comprising a third piece and a fourth piece, wherein:
- the third piece is sized and configured to fit over at least an anterior portion of the upper gum,
- the fourth piece, which is detachably coupled to the third piece, is sized and configured to fit over a posterior portion of the upper gum, and
- the third piece is configured to be inserted into the patient's mouth with the fourth piece attached or without the fourth piece attached; and an intra-oral tracer that is configured to be detachably coupled to the first piece of the lower tray, the intra-oral tracer comprising an edge portion that is inserted into the receiving portion of the first piece, wherein the intra-oral tracer is coupled to the first piece such that an open space of the U-shaped area is substantially covered by the intra-oral tracer, wherein the intra-oral tracer is further configured to be placed between the third piece and the first piece in the mouth when the third piece and the first piece with the intra-oral tracer coupled thereto are inserted into the mouth together, the intra-oral tracer comprising a hole and an adjustable member that is inserted into the hole to be raised or lowered through the hole to determine a vertical dimension, wherein a size of the lower tray including the first piece and the pair of second pieces and a size of the upper tray including the third piece and the fourth piece are fixed, and wherein the first piece of the lower tray with the intra-oral tray attached and the third piece of the upper tray are sized and configured to be inserted together into the mouth to determine jaw relations comprising a vertical dimension and a centric relation.

23. The assembly of claim 22, wherein a first end portion and a second end portion of the first piece is configured to receive corresponding one of the pair of second pieces to be assembled as the lower tray, and the third piece is configured to receive the fourth piece to be assembled as the upper tray.

* * * * *